United States Patent [19]

Buser

[11] 4,226,119
[45] Oct. 7, 1980

[54] SAMPLE INTRODUCTION SYSTEM

[75] Inventor: Hansueli Buser, Arlesheim, Switzerland

[73] Assignee: Ciba-Geigy Corporation, Ardsley, N.Y.

[21] Appl. No.: 956,114

[22] Filed: Oct. 30, 1978

[30] Foreign Application Priority Data

Nov. 3, 1977 [CH] Switzerland ............... 13390/77
Nov. 25, 1977 [CH] Switzerland ............... 14480/77

[51] Int. Cl.³ .............................................. G01N 1/28
[52] U.S. Cl. ............................................. 73/422 GC
[58] Field of Search ................................. 73/422 GC

[56] References Cited

U.S. PATENT DOCUMENTS

| 2,841,005 | 7/1958 | Goggeshall | 73/422 GC |
| 3,672,227 | 6/1972 | Frank | 73/422 GC |
| 3,783,694 | 1/1974 | Otte et al. | 73/422 GC |

FOREIGN PATENT DOCUMENTS 1934487 7/1969 Fed. Rep. of Germany ..... 73/422 GC
2530879 1/1976 Fed. Rep. of Germany .

Primary Examiner—S. Clement Swisher
Attorney, Agent, or Firm—Harry Falber

[57] ABSTRACT

A sample introduction system for a gas chromatograph having a chamber containing a needle for piercing a sample held in a holder and introduced into the chamber via a lock. The needle has a conical point into which a passageway opens perpendicular thereto, the passageway communicating directly with a separating column connected to the chamber. The needle is so shaped that as the sample is pushed onto the point over the entrance to the passageway the sample is sealed against the conical surface and on further penetration of the needle a gap is formed between the needle and the sample to allow ingress of a carrier gas supplied to the chamber.

11 Claims, 8 Drawing Figures

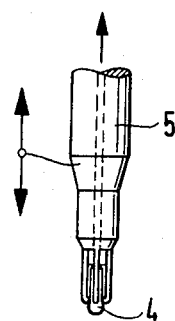
Fig.1
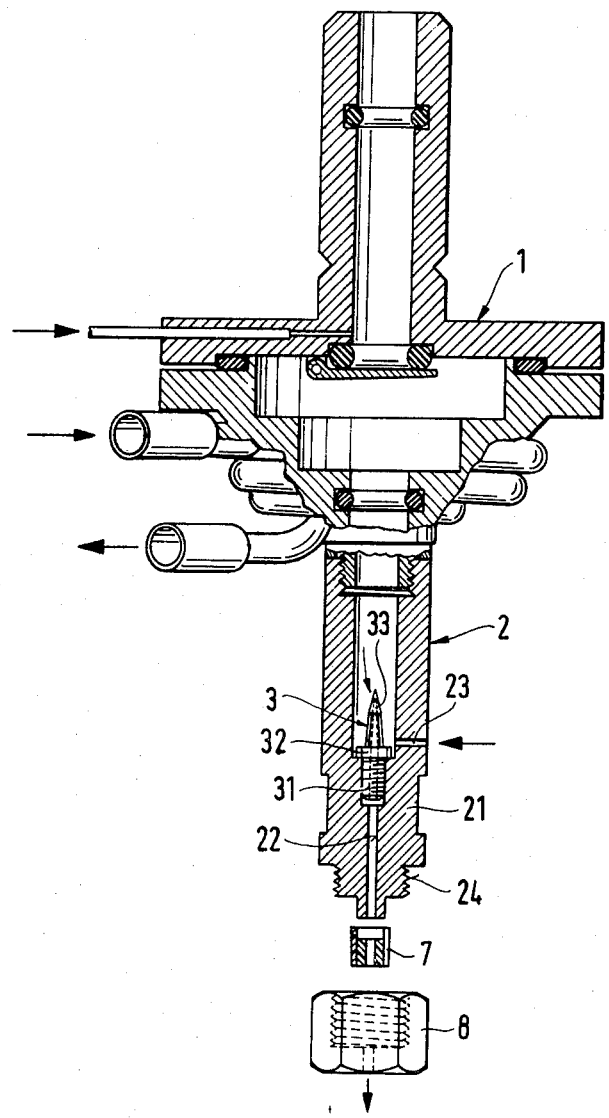

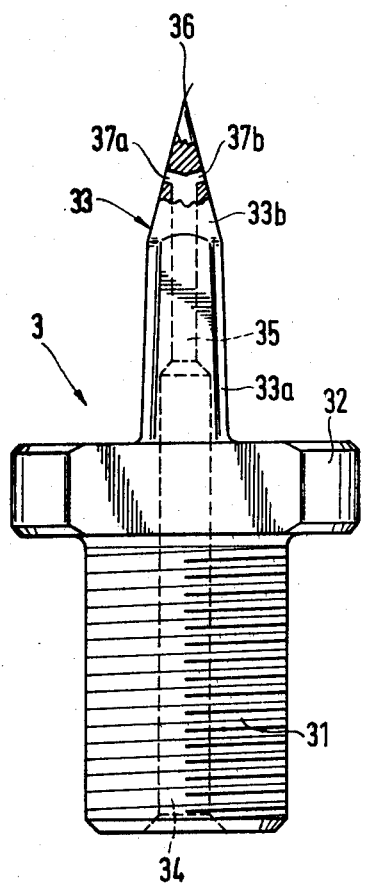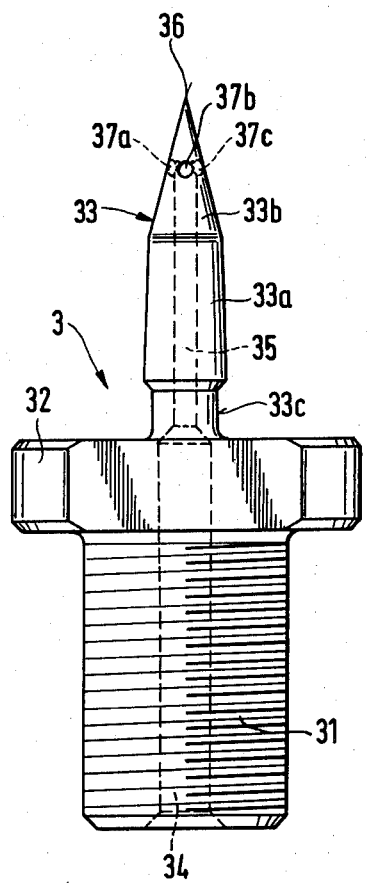
Fig.3  Fig.4
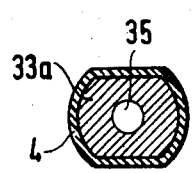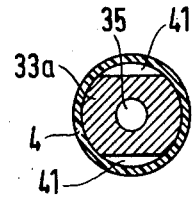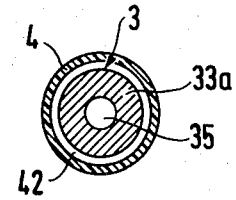
Fig.5a  Fig.5b  Fig.5c

SAMPLE INTRODUCTION SYSTEM

FIELD OF THE INVENTION

This invention relates to a sample introduction system for a gas chromatograph which has a chamber containing a hollow sample capsule receiving needle with an inlet aperture for the sample and carrier gas, the chamber having a connection for a separating column which communicates with the needle, and a connection for carrier gas. The system also includes a lock provided upstream of the chamber and through which the sample capsules are introduced into the chamber by means of a sample holder. The sample capsules are opened by being pushed on to the needle.

PRIOR ART

A system of this kind is described, for example, in DOS No. 25 30 879 and is available from Messrs. Perkin-Elmer Corp. Norwalk, U.S.A., under the name MS 41.

These known sample introduction systems are used practically solely for gas chromatographs with packed columns where they have proved most satisfactory. No comparable sample introduction system appears to exist for capillary gas chromatographs although attempts have long been made to find a way of introducing into the column the substance for analysis unsplit and as far as possible without prior evaporation. Although there has been no lack of proposed solutions to this problem, they are at best only partially satisfactory.

Pages 21 et seq. of "Chromatography Newsletter" Vol. 5, No. 2, 1977 of the Perkin Elmer Corp. describe the use of the above sample introduction system in conjunction with a relatively wide capillary column. However, the carrier gas currents used for capillary columns are unusually high and result in a considerable deterioration of the separating capacity of the capillary column.

It has been found in practice that the known system can be directly applied to capillary gas chromatographs at best only in special cases and with the disadvantage of a considerable loss of separating capacity. The known system cannot be used for normal cases and, in particular, when the very high separating capacity of modern capillary columns is to be or must be fully utilized. The reasons for this lie in the relatively large dead spaces between the receiving needle and the beginning of the separating column and in the needle structure, which is unsuitable for the very low carrier gas currents in the case of capillary gas chromatographs.

OBJECT OF THE INVENTION

The object of the invention, accordingly, is to provide a sample introduction system which permits unsplit injection under isothermal operating conditions, in particular in capillary gas chromatographs without diminishing the specific separating capacity.

SUMMARY OF THE INVENTION

According to the invention the receiving needle is substantially conical or pyramidal, the needle entry opening is disposed in the top quarter of the needle and leads into the needle generatrix, the needle being so shaped that it closes the capsules, so that they are least approximately sealed during penetration of the needle into the capsule to a predetermined depth and frees or creates an access for carrier gas to the capsules on further penetration of the needle. Alternatively, access for the carrier gas is provided by relative rotation of the needle about its axis with respect to the capsules. The column connection is, preferably, so constructed that the column extends directly as far as or into the needle, and the connecting cavities from the needle inlet opening to the opening in the column have substantially the same inside cross-section as the column.

The construction of the receiving needle according to the invention allows the sample capsules to be pushed on to the needle without any appreciable "brow" formation and, in particular, without the contents of the capsule escaping. Since the capillary column extends as far as or even into the needle large dead spaces are avoided so that minimum carrier gas flows can be used, this naturally being to the benefit of the resolution of the chromatograms.

Preferred embodiments of the invention are explained in detail hereinafter with reference to the accompanying drawings wherein:

BRIEF DESCRIPTION OF THE DRAWINGS

FIG. 1 is a longitudinal section through one embodiment of a system according to the invention;

FIGS. 3 and 4 show two forms of receiving needles;

FIGS. 5a and 5b are diagrammatic sections of the line V—V in FIG. 2 with the sample holder turned into two different positions.

FIG. 5c is a similar section to FIG. 5a of a receiving needle of the form shown in FIG. 4.

DETAILED DESCRIPTION OF PREFERRED EMBODIMENTS

Figure 2:
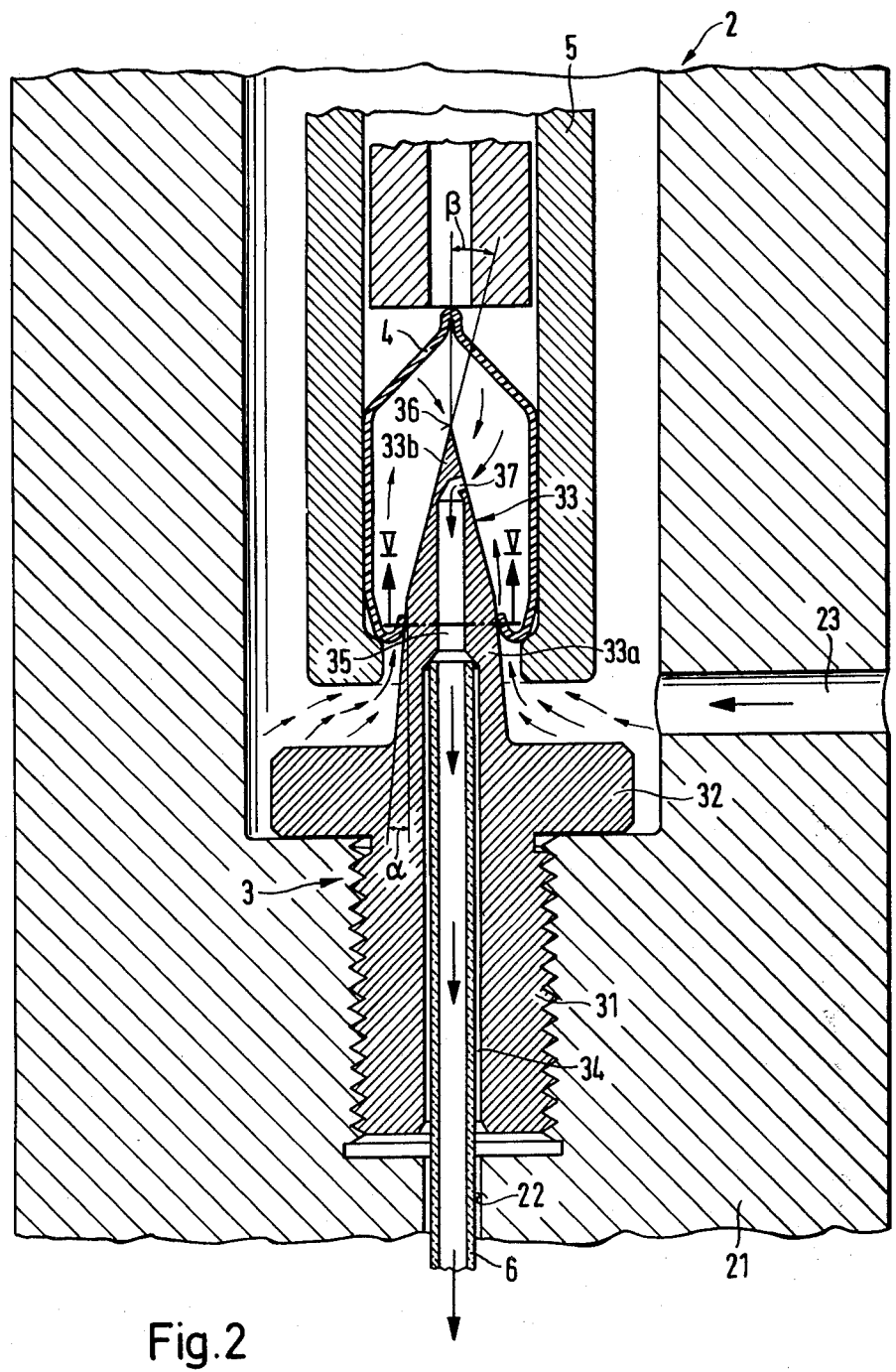
FIG. 2 is a detail of FIG. 1.

The sample introduction system shown as a whole in FIG. 1 comprises a lock 1 followed by a chamber 2 with a receiving needle 3 for a sample capsule 4 which is fixed at the front end of a sample holder 5, only partially shown. Apart from the chamber 2 and the needle 3, all the parts of the sample introduction system illustrated are as described in the above mentioned Perkin-Elmer Corp. MS 41 and in DOS No. 25 30 879.

The chamber 2 formed by a beaker-shaped part is bolted to the lock 1. The receiving needle 3 is screwed into the bottom part 21 of the chamber 2, which contains an axial passage 22, through which the front end of a separating column (FIG. 2) is introduced into the needle 3 in the manner to be described hereinafter. A clamp sleeve 7 and a retaining nut 8 are provided to fix the column in the base part, the nut being adapted to be screwed on to a matching thread 24 on bottom part 21.

FIG. 2 shows the construction of the needle 3 to an enlarged scale. It comprises a base 31 mounted in a screw-threaded passage in the chamber base 21 and having a flange 32, together with a conical or pyramidal point 33 forming the actual needle.

The periphery of the flange 32 is partly bevelled or hexagonal, so that an appropriate shaped spanner can engage it to screw the needle in and out.

The point 33 is divided up into a bottom part 33a and a top part 33b. The angle of inclination $\alpha$ of the generatrices of the bottom part is about 1° to 5°, preferably about 2.5°, and the corresponding angle $\beta$ of the top part of the needle is about 10° to 20°, preferably about 15°. The cross-section of the bottom part 33a is as shown in FIG. 5 and comprises two opposite flats coupled by arcuate portions of substantially the same radius of curvature. A side view of the bottom part 33a showing one of the flats is illustrated in FIG. 3.

The needle has two axial aligned contiguous passages 34 and 35, the thinner one of which extends practically to the tip 36 of the needle point 33. Another passage 37 branches from the end of the passage 35 and extends perpendicularly into the generatrix of the top part 33 of the needle. The larger one of the two axial passages i.e. passage 34, extends to the bottom part 33a of the needle and accommodates the front end of the column 6. The diameter of the thinner axial passage 35 is equal to the inside diameter of the column 6, i.e. about 0.3 to 0.5 mm in the case of a capillary column. In this way, the dead volume between the opening 37 and the column inlet is minimal.

To charge the column 6 with a sample, the capsule 4 containing the sample is introduced through the lock 1 into the chamber 2 by means of the sample holder 5, and pushed on to the needle 3. The needle point 33 penetrates the capsule 4, but seals it off hermetically on all sides as shown in FIG. 5a. The carrier gas entering through the carrier gas inlet 23 disposed level with the bottom part 33a of the needle cannot therefore initially enter the capsule 4, nor can the substance in the capsule escape therefrom into the chamber 2. The capsule 4 is then rotated through 90° about its longitudinal axis by means of the holder 5. As a result of the non-circular cross-section of the bottom part 33a of the needle, the capsule opening is widened out so that entry apertures 41 for the carrier gas form at the flats of the needle (see FIG. 5b) and the carrier gas can now enter the capsule 4 through the apertures so formed and displace the substance therein through the passage 37 into the needle and then into the capillary column 6.

For optimum emptying of the capsule and optimum introduction of the substance into the capillary column, the opening 37 of the needle 33 must be situated as close as possible to the needle tip 36. It is not advisable to dispose the opening 37 directly at the tip 36, because of the risk of clogging. In practice it is sufficient for the opening to be in the top quarter or fifth of the needle point 33, i.e. the distance between the flange 32 and the tip 36. The opening should also be as small as possible when measured in the direction of the generatrix. The passage 37 thus extends perpendicularly to the generatrix for this reason.

Instead of providing a single passage, a plurality thereof, e.g. two or three, may be advantageously provided. FIG. 3 shows a needle with two passages. The two passages 37a and 37b are diametrically opposite one another and each are offset by 90° with respect to the flats on the bottom part of the needle. This gives very intensive flushing out of the capsule.

The fact that the needle point is divided into a top part having an opening angle which is large relative to the opening angle of the bottom part, the correct dimensions for these angles are of importance for optimum emptying of the capsule. This avoids "brows" which would result in the formation of pockets in the capsule in which the substance might collect. It has also been found advantageous for at least the lower edge of the orifice(s) of the passage(s) 37 to be rounded off. This facilitates clean piercing of the capsule and prevents the edge of the capsule opening from fraying as it slides over the opening 37.

Another important factor for the application of capsule technique to capillary columns is that the needle should be so devised as to seal off the capsule until the full penetration depth is reached, and only then allow access for the carrier gas. As already described this can be achieved, for example, by providing flats or bevelling the bottom part 33a of the needle. The needle could also have a polygonal cross-section in its bottom part for this purpose. FIG. 4 shows another suitable form of needle, having a point which is symmetrical with respect to its rotational axis and which has a bottom and top part 33a, 33b, respectively. The top part 33b has three passages or openings 37a, b and c. Instead of providing flats or bevelled surfaces of the needles as shown in FIGS. 2 and 3, a constriction of the cross-section or annular groove 33c is provided at the bottom end of the needle point. When, on insertion of the needle the edge of the capsule opening reaches the annular groove, an annular gap 42 abruptly forms through which the carrier gas can then flow into the capsule. This is shown in simplified form in FIG. 5c. Instead of the annular groove, notches or recesses distributed over the periphery of the bottom part of the needle may be provided.

Figure 6:
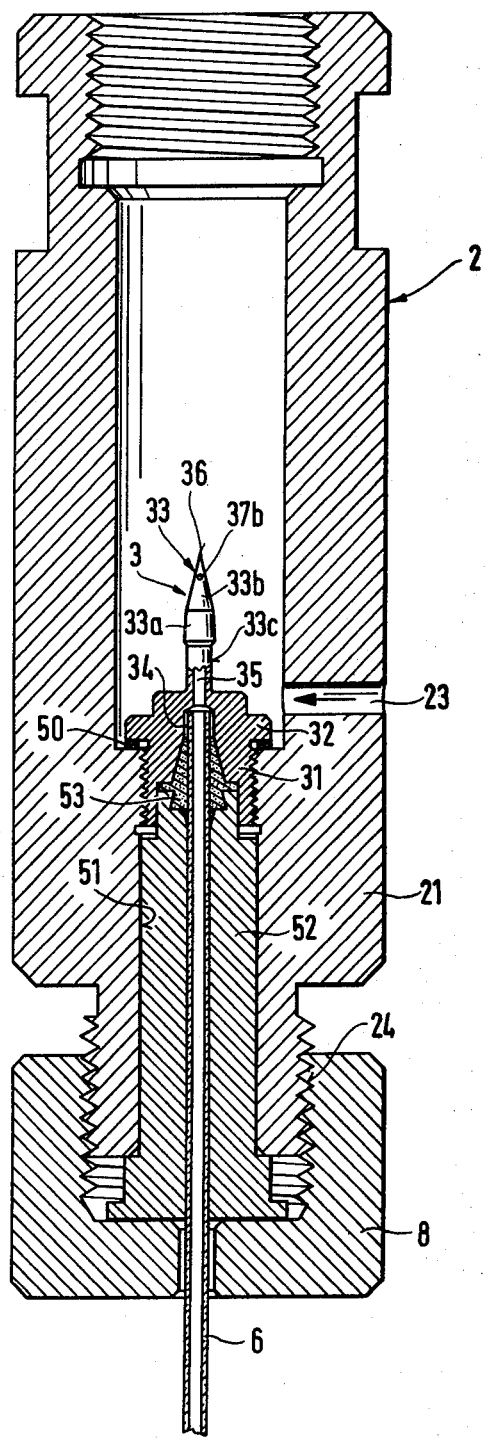
FIG. 6 shows in detail the fixing of the capillary column.

FIG. 6 shows the fixing of the capillary column 6 in the base of the chamber in greater detail. The needle 3 is screwed into the base 21 of the chamber 2 and sealed by means of a silver gasket 50. A lining tube 52, which encloses and protects the capillary 6, is mounted in the passage 51 in the chamber base 21. A graphite ferrule 53 is provided at the front end of the tube 52 and its conical surfaces ensure a sealing-tight connection between the tube 52 and the bottom part of the needle. The tube is fixed to the chamber base 21 by means of the retaining nut 8.

The capillary fixing shown in FIG. 6 gives minimum dead volumes and also prevents any breakage of the capillary on introduction into the needle.

The above-described sample introduction system enables the capsule technique which was hitherto possible only for packed columns, apart from the exceptions indicated, to be applied for the first time to high-performance capillary columns without any impairment of the separation capacity. The system is designed primarily for capillary columns but, is also suitable and advantageous for packed columns.

I claim:

1. A sample introduction system for a gas chromatograph comprising:
   (a) a chamber;
   (b) a lock on said chamber;
   (c) an inlet for introducing carrier gas to said chamber;
   (d) a separating column;
   (e) a needle mounted in said chamber, said needle having a conical top part which converges upwards to a point, a bottom part having surfaces which converge upwards towards said top part and wherein the generatrices of the bottom part are at a smaller angle to the needle axis than the generatrix of the top part, and a passage extending from said bottom part up through said top part to emerge at an opening in the surface thereof, said bottom part having a bore to receive said separating column and communicating directly with said passageway; and
   (f) a sample holder mounted to introduce a sample via said lock into said chamber and onto said needle in sealing engagement with the surface of said top part, the bottom part of said needle having a configuration such that when said sample reaches said bottom part a gap is formed therebetween to allow carrier gas introduced via said inlet to enter said sample.

2. A system according to claim 1, wherein said bottom part has flats formed thereon so that relative rotation of said needle and said holder forms said gap when the sample has been pushed over said bottom part.

3. A system according to claim 1, wherein said bottom part has a recess therein to form said gap when said sample is pushed onto the bottom part of said needle.

4. A system according to claim 1, wherein the angle of the generatrix of the top part relative to the needle axis is in the range 10° to 20°.

5. A system according to claim 4, wherein the angle of the generatrices of the bottom part relative to the needle axis are in the range 1° to 5°.

6. A system according to claim 1, wherein the passage has a diameter substantially the same as the inner diameter of said separating column.

7. A sample introduction system for gas chromatograph comprising:
(a) a chamber;
(b) a lock on said chamber;
(c) an inlet for introducing carrier gas to said chamber;
(d) a separating column;
(e) a needle mounted in said chamber, said needle having a conical top part, a bottom part, and a passage extending from said bottom part up through said top part to emerge perpendicular to the surface thereof in an opening therein, said bottom part having surfaces which converge upwards towards said top part and wherein the generatrices of the bottom part are at a smaller angle to the needle axis than the generatrix of the top part, and having a bore to receive said separating column and communicating directly with said passageway; and
(f) a sample holder mounted to introduce a sample via said lock into said chamber and onto said needle in sealing engagement with the surface of said top part, the bottom part of said needle having a configuration such that when said sample reaches said bottom part a gap is formed therebetween to allow carrier gas introduced via said inlet to enter said sample.

8. A system according to claim 7, wherein said top part defines two openings in the surface thereof, each communicating with said passageway.

9. A system according to claim 7, wherein said opening is in the top fifth of the needle.

10. A system according to claim 9, wherein said carrier gas inlet is located in the chamber level with the bottom part of said needle.

11. A system according to claim 7, wherein the passage has a diameter substantially the same as the inner diameter of said separating column.

* * * * *